United States Patent [19]

Kawaguchi et al.

[11] Patent Number: 4,891,972
[45] Date of Patent: * Jan. 9, 1990

[54] ULTRASONIC JOINT INSPECTION DEVICE AND METHOD

[75] Inventors: Takashi Kawaguchi, Ageo; Yoshiaki Fujita, Omiya; Satoshi Kawai, Tochigi, all of Japan

[73] Assignee: Nippon Piston-Ring Co., Ltd., Tokyo, Japan

[*] Notice: The portion of the term of this patent subsequent to Apr. 4, 2006 has been disclaimed.

[21] Appl. No.: 254,168

[22] Filed: Oct. 6, 1988

Related U.S. Application Data

[63] Continuation of Ser. No. 113,354, Oct. 28, 1987, Pat. No. 4,817,420, which is a continuation of Ser. No. 873,948, Aug. 20, 1986, abandoned.

[30] Foreign Application Priority Data

Jun. 14, 1985 [JP] Japan ................................ 60-127979

[51] Int. Cl.$^4$ .......................................... G01M 15/00
[52] U.S. Cl. .................................... 73/119 R; 73/623
[58] Field of Search ................... 73/119 R, 598, 600, 73/623, 629, 618, 634, 866.5, 638, 637, 639, 622, 633, 620, 596, 584, 570, 627, 624, 625; 123/90.6

[56] References Cited

U.S. PATENT DOCUMENTS

| | | |
|---|---|---|
| 3,289,468 | 12/1966 | Van Der Veer et al. |
| 3,508,436 | 4/1970 | Krautkramer |
| 4,008,603 | 2/1977 | Paulissen |
| 4,037,465 | 7/1977 | Cook et al. |
| 4,041,773 | 8/1977 | Hauldren et al. |
| 4,123,943 | 11/1978 | Roddy et al. |
| 4,212,207 | 7/1980 | Conradi |
| 4,265,388 | 5/1981 | Takahashi et al. |
| 4,361,044 | 11/1982 | Kupperman et al. |
| 4,549,426 | 10/1985 | Erickson ................................ 73/3 |
| 4,593,568 | 6/1986 | Telford et al. |

FOREIGN PATENT DOCUMENTS

| | | |
|---|---|---|
| 1217886 | 5/1960 | France |
| 2214379 | 8/1974 | France |
| 862561 | 3/1961 | United Kingdom |

Primary Examiner—Robert R. Raevis
Attorney, Agent, or Firm—Birch, Stewart, Kolasch & Birch

[57] ABSTRACT

A method and device for the examination of a joint between a hollow steel shaft and a piece joined to the steel hollow shaft of a composite camshaft using ultrasonic examination. In the ultrasonic examination, the composite camshaft is put into a liquid and a probe of an ultrasonic search unit is inserted inside of the hollow steel shaft. The ultraonic examination of the joint is performed from inside of the hollow steel shaft. According to the ultrasonic examination, any kind of joint of the composite camshaft is possible, because a distance from an inside surface of the hollow steel shaft to the joint is constant. In addition, since the probe does not contact the inside surface of the hollow steel shaft, the probe is not consumed due to abrasion.

4 Claims, 2 Drawing Sheets

ULTRASONIC JOINT INSPECTION DEVICE AND METHOD

This application is a continuation of copending application Ser. No. 07/113,354, filed on Oct. 28, 1987, now Pat. No. 4,817,420, which is a continuation of application Ser. No. 06/873,948 filed on Jun. 13, 1986, now abandoned.

BACKGROUND OF THE INVENTION

1. Field of the Invention:

The present invention relates to a method and device for inspection or examination of a joint between a steel shaft and a piece to be joined to the steel shaft of a composite camshaft.

2. Description of the Prior Art:

A composite camshaft having a steel shaft and a piece joined to the shaft is well known. In the composite camshaft, an element such as a cam, a journal, a gear and a fitting means for a spanner is constructed of a part independent of the shaft of the composite camshaft and then the piece is fitted to the shaft and is integrally joined to the shaft. Japanese Utility Model Publication 51-7367 discloses a composite camshaft of this kind in which at least one of a cam and a camshaft is constructed of a sintered metal and then is integrally joined to the steel shaft through diffusion by sintering.

In a composite camshaft, the piece to be joined to a shaft is not limited to a sintered metal and may be constructed of steel. In the case the piece is constructed of steel, the steel piece is usually joined to the steel shaft through braze welding or solder welding. In such a composite camshaft, the joint between the piece with the shaft should be examined and be confirmed to be of high quality and strength.

As a method for examination of the joint of the composite camshaft there is presently utilized a destructive examination in which the composite camshaft is cut and the exposed surface is examined by sight. However, such a destructive examination requires much time and expense.

Recently, an ultrasonic examination has been applied to the examination of the joint of a composite camshaft in which a probe of an ultrasonic search unit is moved along the joined piece with the probe in direct contact with the outside surface of the joined piece. However, such an ultrasonic examination requires a considerable amount of time and results in the consumption of the probe and therefore, is not deemed economically appropriate. In addition, since the ultrasonic examination is applied from outside of the composite camshaft and since the distance from the outside surface of the joined piece to the joint varies in the circumferential direction of the cam due to the radial distance difference between the base circle portion and the cam nose of the cam, the quality of the examination is of a low grade. Further, since the ultrasonic wave beams do not transmit straight at the surface of the cam nose in the case of the cam, the examination of the portion of the joint corresponding to the cam nose has been impossible.

SUMMARY OF THE INVENTION

An object of the present invention is to provide a method and device for the nondestructive examination of the joint of a composite camshaft, in which a probe of a search unit is not consumed due to abrasion with the composite camshaft to be examined and the examination of a portion of the joint corresponding to a cam nose is possible.

The above described object can be achieved, according to the present invention, by a method for examination of a joint between a hollow steel shaft and a piece joined to the outside surface of the hollow steel shaft of a composite camshaft including the steps of (1) putting the composite camshaft into a liquid, (2) inserting a probe of an ultrasonic search unit inside of the hollow steel shaft, and (3) applying an ultrasonic examination to the joint from inside of the hollow steel shaft.

Also, the above-described object can be achieved, according to the present invention, by a device for examination of a joint of the hollow steel shaft and a piece joined to the outside surface of the hollow steel shaft of a composite camshaft including (1) providing a liquid in which the composite camshaft is placed, and (2) providing a probe of an ultrasonic search unit placed in the liquid and inside of the hollow steel shaft. Advantageously, the device further comprises (3) a mirror for reflecting ultrasonic wave beams coming from the probe toward the joint and echoes returning from the joint toward the probe, (4) means for driving the mirror in an axial direction of the probe, and (5) means for rotating either one of the composite camshaft and the mirror.

According to the above-described method and device, the probe of the ultrasonic search unit is not brought into direct contact with the inside surface of the hollow steel shaft, and thus the probe is not consumed at all due to abrasion with the inside surface of the shaft.

In addition, since the ultrasonic examination of the joint between the piece and the hollow steel shaft is performed from the inside of the hollow steel shaft, the distance from the inside surface of the hollow steel shaft to the joint is constant in the circumferential direction of the composite camshaft and thus the whole joint can be examined without receiving any influence from the variance in the distances between the outside surface of the cam and the joint. As a result, a high quality of examination can be obtained.

BRIEF DESCRIPTION OF THE DRAWINGS

These and other objects and advantages of the invention will become apparent and more readily appreciated from the following description of the presently preferred exemplary embodiments of the invention taken in conjunction with the accompanying drawings, wherein.

DESCRIPTION OF THE PREFERRED EMBODIMENT

Figure 1:
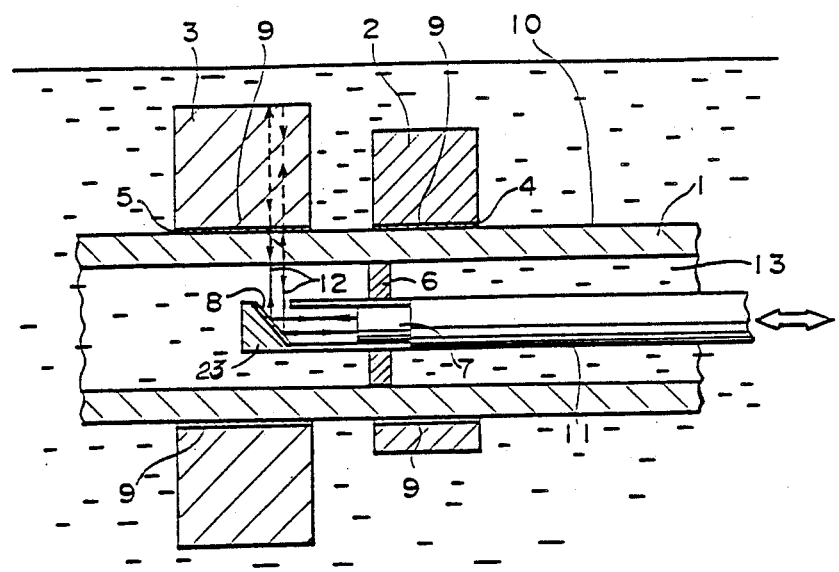
FIG. 1 is a partial sectional view of a device for the examination of a joint of a composite camshaft in accordance with the present invention.

FIGS. 1 to 6 show an ultrasonic inspection device in accordance with the present invention. A composite camshaft 10 comprises a hollow steel shaft 1, at least one end of which is opened during examination. To an outside surface of hollow steel shaft 1 a piece such as a cam 2 and/or a journal 3 is joined. Cam 2 is constructed of, for example, sintered metal and journal 3 is constructed of, for example, steel. The piece may be a gear 31 and/or a fitting 32 for a spanner shown in FIG. 6. In the above example, cam 2 may be a steel cam and journal 3 may be a sintered metal. In case the piece is a sintered metal, a joint 4 between the piece and hollow steel shaft 1 is constructed by sintering and the piece is integrally connected to the outside surface of hollow steel shaft 1 through diffusion by sintering. In case the piece is a steel one, a joint 5 is constructed by braze welding or solder welding. Joint 4 by sintering and joint 5 by braze welding or solder welding constitute a joint 9 to be examined in the present invention.

Figure 4:
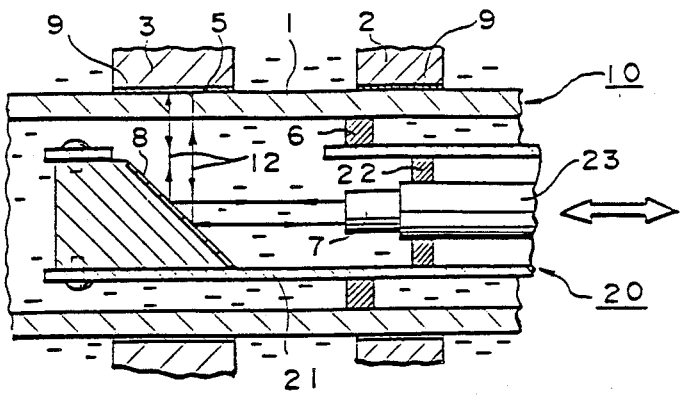
FIG. 4 is a partial sectional view of a device for rotatably supporting a mirror which is used when the mirror is rotated during the examination.

A probe 7 of an ultrasonic inspection device 11 is inserted into hollow steel shaft 1. Probe 7 is mounted within a support shaft 23 and is slidable and rotatable with respect to steel hollow shaft 1 by means of a probe guide 6 which is interposed between support shaft 23 and steel hollow shaft 1. Probe 7 penetrates probe guide 6 and is arranged coaxially with the inside surface of hollow steel shaft 1. In FIG. 4, probe guide 6 is constructed of a bearing. A mirror 8 for reflecting ultrasonic wave beams from probe 7 toward joint 9 and echoes from joint 9 to probe 7 in a right angle manner is provided in front of probe 7 and opposed to probe 7. Reference numeral 12 shows ultrasonic wave beams and echoes thereof.

The ultrasonic examination of joint 9 is performed in a liquid 13 such as water or oil in a tank. Liquid 13 may include a rust preventive.

Figure 2:
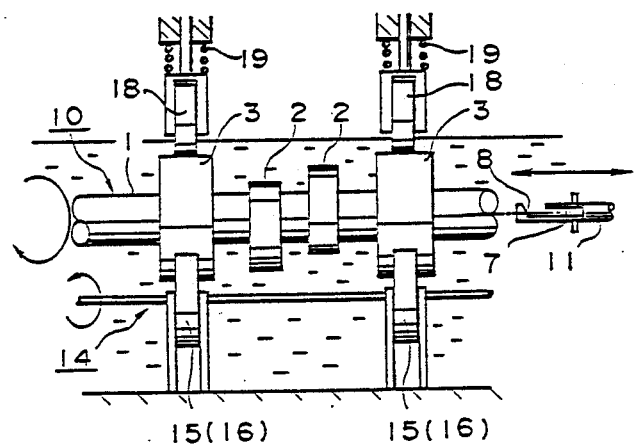
FIG. 2 is a partial elevational view of a device for rotating the composite camshaft which is used when the composite camshaft is rotated during the examination.
Figure 3:
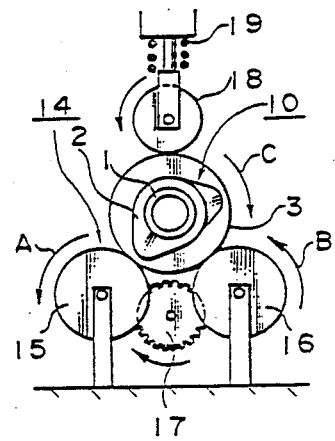
FIG. 3 is a side view of the device of FIG. 2.

The inspection device further comprises means for rotating either one of composite camshaft 10 and mirror 8. FIGS. 2 and 3 show a device which is used when composite camshaft 10 is rotated during examination. Means 14 for rotating composite camshaft 10 comprises a first roller 15 and a second roller 16 which are in parallel with each other and are driven in the same direction of arrows A and B. Rollers 15 and 16 are coupled with each other via a gear 17 interposed between rollers 15 and 16. Rollers 15 and 16 are driven by an A.C. variable speed motor (not shown). Composite camshaft 10 is mounted on rollers 15 and 16 and is driven in a direction of arrow C by rollers 15 and 16. Composite camshaft 10 is slightly pushed downward by a third roller 18 which is elastically supported by means of a spring 19. Roller 18 prevents composite camshaft 10 from moving out of position when rotated.

FIG. 4 shows a device which is used when mirror 8 is rotated during examination. Means 20 for rotating mirror 8 includes a rotating shaft 21, to the end of which, mirror 8 is fixed. A bearing 22 is interposed between rotating shaft 21 and a supporting shaft 23, at an end of which, probe 7 is supported. Bearing 22 allows mutual rotation of mirror 8 with respect to probe 7. Rotating shaft 21 is driven to rotate by means of an A.C. variable speed motor (not shown).

Figure 7:
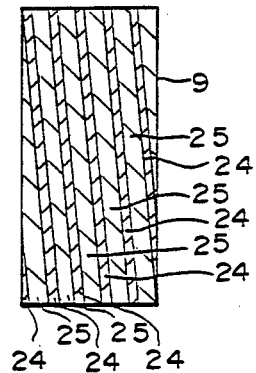
FIG. 7 is a developed view of the joint showing scanning states when either one of the composite camshaft and the mirror is rotated at a high speed.
Figure 8:
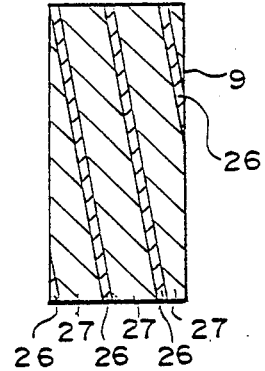
FIG. 8 is a developed view of the joint showing scanning states when either one of the composite camshaft and the mirror is rotated at a low speed.

Mirror 8 is movable in an axial direction of probe 7, that is, in an axial direction of composite camshaft 10 by means of a pulse motor (not shown). Mirror 8 moves together with probe 7 in the axial direction. FIG. 7 shows scanning bands 24 and 25 when either one of composite camshaft 10 and mirror 8 is rotated at a relatively high speed. Band 24 shows a width of ultrasonic wave beams 12 and band 25 shows an area scanned by one pitch axial movement of mirror 8 during one relative rotation between composite camshaft 10 and mirror 8. The pitch of the axial movement of mirror 8 is adjusted to scan the whole area of joint 9 as shown in FIG. 7. FIG. 8 shows scanning bands 26 and 27 when either one of composite camshaft 10 and mirror 8 is rotated at a relatively low speed. Band 26 shows a width of ultrasonic wave beams 12 and band 27 shows an area scanned by one pitch axial movement of mirror 8 during one relative rotation between composite camshaft 10 and mirror 8. Band 27 under low speed operation is wider than band 25 under high speed operation due to a greater number of scanning cycles per unit length of movement along the longitudinal axis of the hollow shaft.

Figure 5:
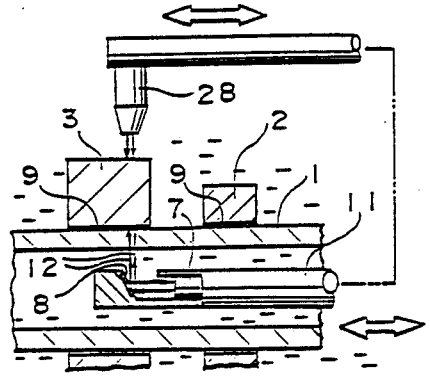
FIG. 5 is a partial sectional view of a device used in determining the relative position of the mirror with respect to the composite camshaft.
Figure 6:
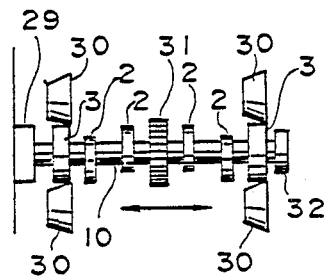
FIG. 6 is a partial elevational view of another device used in determining the relative position of the mirror with respect to the composite camshaft.

FIGS. 5 and 6 show devices for determining a position of a portion of joint 9 to be searched. In the device of FIG. 5, a sub-probe 28 is provided outside of composite camshaft 10. Sub-probe 28 is positioned to correspond to mirror 8 in an axial direction of probe 7 and can move together with mirror 8 in the axial direction of probe 7. Since the position of sub-probe 28 can be determined by ultrasonic wave beams which are issued from sub-probe 28, and are reflected by the outside surface of the piece joined to hollow steel shaft 1 toward sub-probe 28 a position of mirror 8 can easily be determined. In the device of FIG. 6, a reference plate 29 is statically provided. In the case mirror 8 is rotated in examination, one end of composite camshaft 10 is butt against reference plate 29. When composite camshaft 10 is rotated in examination, composite camshaft 10 is pushed by means of taper roller 30 in one direction and one end of composite camshaft 10 is butt against reference plate 29. Data about distances from reference plate 29 to each joint 9 are in the memory of the data processing unit (not shown) and the position of joint 9 under examination can be easily recognized on the basis of the information from the data processing unit.

Using the above device, the method for examination of the joint 9 according to the present invention is performed as mentioned below. At first, the tank including probe 7 and mirror 8 therein is filled with liquid 13 such as water or oil. Next, composite camshaft 10 is placed into liquid 13. In the case composite camshaft 10 is rotated during examination, composite camshaft 10 is supported by first and second rollers 15 and 16 and biased by third roller 18. Then, probe 7 and mirror 8 are inserted inside of hollow steel shaft 1 of composite camshaft 10. Then either one of composite camshaft 10 and mirror 8 is rotated and at the same time the ultrasonic examination is applied to joint 9 to be examined from inside of hollow steel shaft 1 of composite camshaft 10. In the case composite camshaft 10 is rotated during examination, composite camshaft 10 is driven by rotation of rollers 15 and 16. In the case mirror 8 is rotated during examination, mirror 8 is driven to rotate by rotating shaft 21. While either one of composite camshaft 10 and mirror 8 is rotated, mirror 8 is driven in the axial direction of probe 7 and scanning shown in FIG. 7 or FIG. 8 is obtained according to the rotational speeds of either one of composite camshaft 10 or mirror 8. In this manner the whole portion of joint 9 is scanned. In examination, ultrasonic wave beams 12 issued from probe 7 are transmitted in liquid 13 to mirror 8 and are reflected by mirror 8 toward joint 9 at a right angle and then are transmitted in liquid 13 to the inside surface of hollow steel shaft 1. At the inside surface of hollow steel shaft 1, one portion of ultrasonic wave beams 12 is reflected in a reverse direction and the echoes return on the same route to probe 7. The other portion of ultrasonic wave beams 12 is transmitted in hollow steel shaft 1 to joint 9. If there is no defects in joint 9, ultrasonic wave beams 12 will go straight to the outside surface of the joined piece. However, if there is any defect in joint 9, ultrasonic wave beams 12 are reflected at the defect and the echoes 12 return on the same route to probe 7. Upon receiving the echoes 12, electric signals corresponding to echoes 12 can be detected by a detective electrical unit (not shown) which is electrically connected to probe 7 and is positioned outside liquid 13.

Next, the effects of the above ultrasonic examination method and device will be explained.

In the ultrasonic examination of the present invention, since probe 7 is accessed from inside of hollow steel shaft 1 where the distance between the inside surface of hollow steel shaft 1 and joint 9 is constant, that is, is equal to the thickness of hollow steel shaft 1, the application of the ultrasonic examination becomes possible to all kinds of joints 9, even if the distance from the outside surface of the piece varies, such as in the case of a cam nose. As a result, the quality of the examination is increased.

Furthermore, since probe 7 is not brought into direct contact with the inside surface of hollow steel shaft 1, abrasion of probe 7 does not occur that would result in the consumption of probe 7 which has a high cost.

Although only a few exemplary embodiments of the present invention have been described in detail above, those skilled in the art will readily appreciate that many modifications are possible in the exemplary embodiments without materially departing from the novel teachings and advantages of the invention. Accordingly, all such modifications are intended to be included within the scope of the present invention as defined in the following claims.

What is claimed is:

1. An ultrasonic joint inspection device for inspecting a joint between a hollow shaft and a piece joined to an outside surface of the hollow shaft of a composite camshaft, said device comprising:
   a probe having means for generating ultrasonic waves and means for detecting ultrasonic waves;
   a mirror positioned in front of said probe in a pathway of said ultrasonic waves generated from said probe for deflecting said ultrasonic waves;
   a sub-probe positioned outside said composite camshaft so as to correspond in position to said mirror in an axial direction of said hollow shaft and operatively coupled to said probe so as to move together with said probe and said mirror;
   support means for supporting and aligning said probe and said mirror;
   guide means for supporting, positioning and aligning an assembled structure of said support means, said probe and said mirror within and out of engagement with an inner peripheral surface of the hollow shaft whereby a precise, fixed distance is maintained between said mirror and the joint being examined during the rotation of the hollow shaft about the inspection device; and
   camshaft support means for supporting and rotating the camshaft being inspected, said camshaft support means comprising:
   a first roller and a second roller rotatably mounted to a support;
   a third roller positioned above said first roller and said second rollers;
   biasing means for biasing said third roller against an outer peripheral surface of the hollow shaft during rotation of the hollow shaft about said probe;
   drive means for driving said rollers for rotating the hollow shaft; and
   means for moving said probe along a longitudinal axis of the hollow shaft for providing scanning of the entire joint.

2. The device according to claim 1, wherein said mirror is planar and is positioned at a 45° angle with respect to a longitudinal axis of said support means.

3. An ultrasonic joint inspection device for inspecting a joint between a hollow shaft and a piece joined to an outside surface of the hollow shaft of a composite camshaft, said device comprising:
   a probe having means for generating ultrasonic waves and means for detecting ultrasonic waves;
   a mirror positioned in front of said probe in a pathway of said ultrasonic waves generated from said probe for deflecting said ultrasonic waves;
   a sub-probe positioned outside said composite camshaft so as to correspond in position to said mirror in an axial direction of said hollow shaft and operatively coupled to said probe so as to move together with said probe and said mirror;
   support means for supporting and aligning said probe and said mirror;
   guide means for supporting, positioning and aligning an assembled structure of said support means, said probe and said mirror within and out of engagement with an inner peripheral surface of the hollow shaft whereby a precise, fixed distance is maintained between said mirror and the joint being examined during the rotation of the hollow shaft about the inspection device; and
   camshaft support means for supporting and rotating the camshaft being inspected, said camshaft support means comprising:
   a first roller and a second roller rotatably mounted to a support; a third roller positioned above said first roller and said second rollers;
   biasing means for biasing said third roller against an outer peripheral surface of the hollow shaft during rotation of the hollow shaft about said probe;
   drive means for driving said rollers for rotating the hollow shaft;
   means for moving said probe along a longitudinal axis of the hollow shaft for providing scanning of the entire joint; and
   said sub-probe includes means for generating ultrasonic waves and means for detecting ultrasonic waves.

4. An ultrasonic joint inspection device for inspecting a joint between a hollow shaft and a piece joined to an outside surface of the hollow shaft of a composite camshaft, said device comprising:
   a tank filled with a coupling liquid;

an ultrasonic probe having means for generating and detecting ultrasonic waves from within the hollow shaft for inspecting the joint;

an ultrasonic sub-probe having means for generating and detecting ultrasonic waves from outside the hollow shaft for determining a position of said probe, said sub-probe being operatively coupled to said probe so as to move together with said probe in an axial direction of the hollow shaft; and camshaft support means for supporting and rotating the camshaft being inspected within said coupling liquid, said camshaft support means comprising:

a first roller and a second roller rotatably supported within said tank;

a third roller positioned above said first roller and said second roller;

biasing means for biasing said third roller against an outer peripheral surface of the hollow shaft during rotation of the hollow shaft about said probe; and drive means for driving said rollers for rotating the hollow shaft.

* * * * *